United States Patent [19]

Lindemann

[11] Patent Number: 4,538,599
[45] Date of Patent: Sep. 3, 1985

[54] ORTHOSIS DEVICE FOR CONGENITAL METATARSUS

[76] Inventor: Peer Lindemann, 1736 Cherokee, West Bend, Wis. 53095

[21] Appl. No.: 549,169
[22] Filed: Nov. 7, 1983
[51] Int. Cl.³ .............................................. A61F 3/00
[52] U.S. Cl. ............................................... 128/80 A
[58] Field of Search .................... 128/80 A, 80 J, 583, 128/584, 585, 592, 581, 80 R

[56] References Cited

U.S. PATENT DOCUMENTS

| 2,967,360 | 1/1961 | Rice | 128/80 J |
| 3,308,829 | 3/1967 | Edwards | 128/80 R |
| 3,413,977 | 12/1968 | Soble et al. | 128/583 |
| 3,762,421 | 10/1973 | Sax | 128/80 A |
| 4,434,792 | 3/1984 | Rosenberg | 128/80 R |

FOREIGN PATENT DOCUMENTS 121322 12/1918 United Kingdom ............ 128/80 A

Primary Examiner—C. Fred Rosenbaum
Assistant Examiner—Christa K. Scott
Attorney, Agent, or Firm—Ira Milton Jones

[57] ABSTRACT

An orthosis device for treatment of congenital metatarsus comprising a shoe having articulated toe and heel portions and means for exerting yielding pressure on the toe portion tending to at all times draw the same laterally outwardly relative to the heel portion.

8 Claims, 6 Drawing Figures

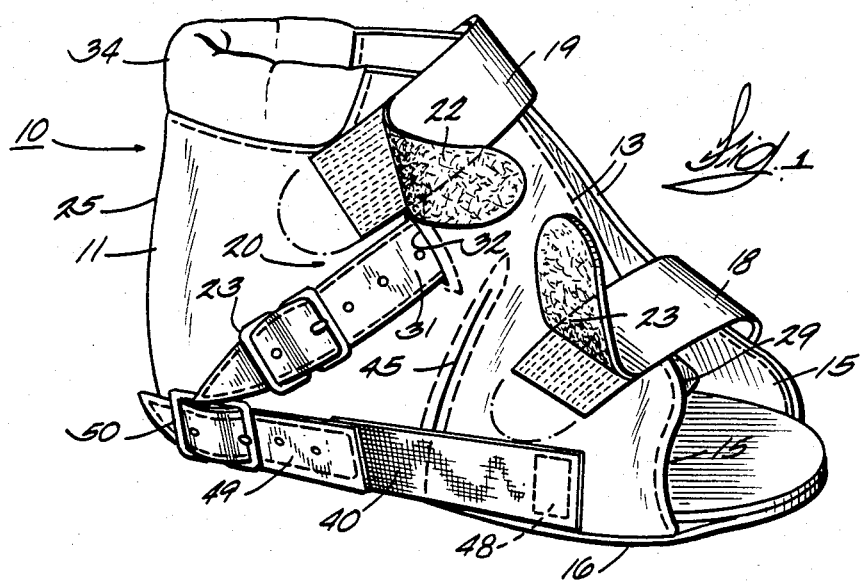
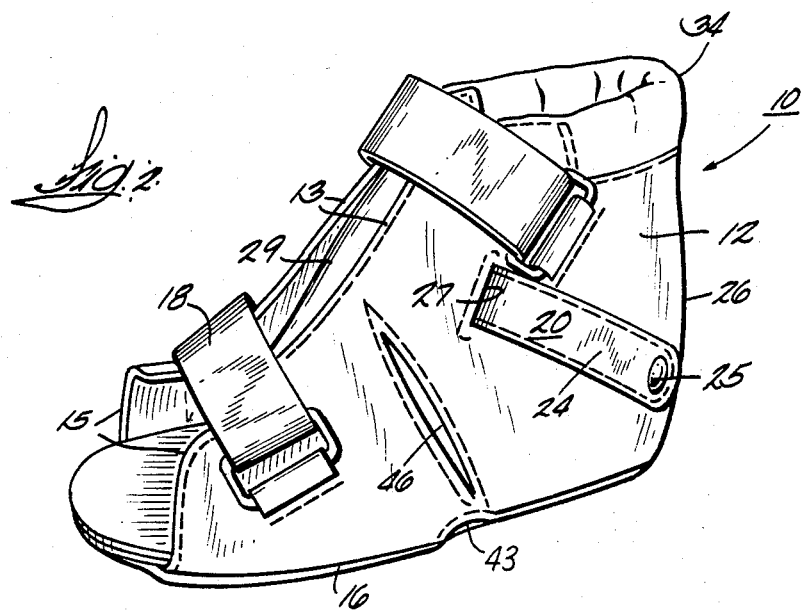

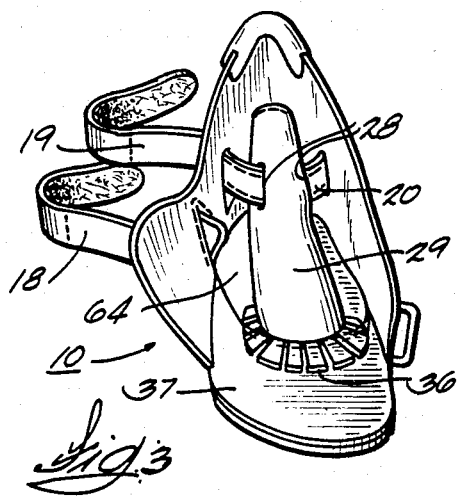
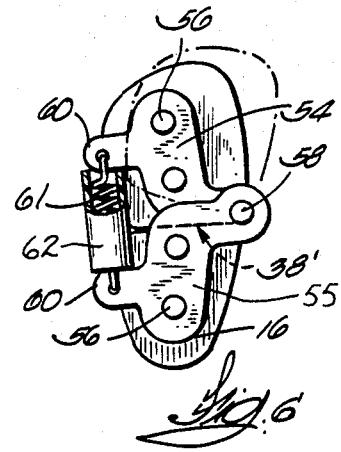
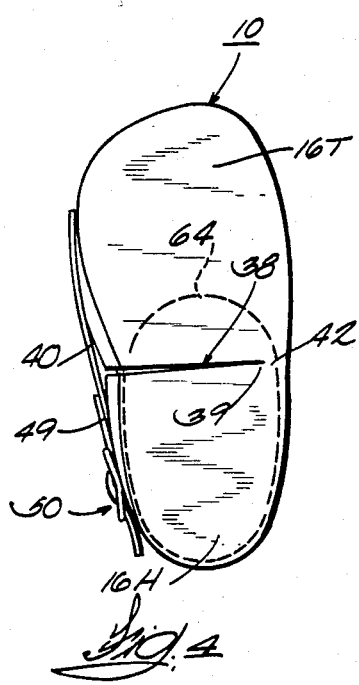
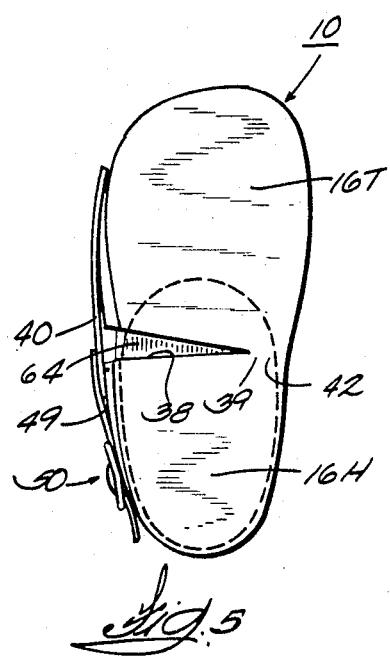

ORTHOSIS DEVICE FOR CONGENITAL METATARSUS

This invention relates to orthosis, or treatment of maladjusted feet, particularly those of children.

Traditional treatment for congenital metatarsus can range from benign neglect for mild cases, to operative intervention for severe, resistant deformities.

In the past, the treatment of choice for the majority of cases has been either manipulation, including stretching exercises, in an effort to correct deformity, and/or static casting in an overcorrected position, or even a combination of both. These conventional treatments have shown varying degrees of effectiveness, but both experience inherent problems.

Manipulation and stretching exercises must be performed on a regular basis and be properly applied to be effective. This requires teaching the parents or others caring for the child, not only the proper manipulative technique but also the diligent application of these techniques on their part. If these techniques are improperly performed or not diligently carried out on a regular basis, the treatment becomes ineffective and casting or surgical intervention will be required. The manipulative technique is very precise and oftentimes is not carried out properly by lay persons.

Further, taping is sometimes used to augment manipulative exercises. However, inherent in taping is a risk of skin breakdown in necrosis and neurovascular impairment.

When static casting is resorted to, the foot is manipulated into an overcorrected position and then immobilized in a cast. While this can be successful, it does encounter potentially serious complications. The risk of pressure sores and plaster burns on tender skin is quite high. A common error in applying the static cast is to apply the plaster to the foot and then manipulate the foot into the overcorrected position. This causes the cast to put pressure on the foot to hold it in position and leads to potentially serious skin breakdown.

Even properly applied casts must be changed at regular intervals to allow for the child's growth and to facilitate inspection and manipulation of the foot. This entails potential psychological trauma to the child and the parents by the noise of the cast saw, along with the very real potential danger of the patient being cut by the saw, or the very difficult and tedious task of soaking casts in acetic acid solution to soften them for unwrapping. Frequent changing of the cast also greatly increases the cost of treatment, as repeated visits and casting by the physician or his staff are required.

There is also danger of injury to the child from the cast, particularly to babies who often kick and crawl about.

This invention overcomes the above mentioned problems previously encountered in the treatment of congenital metatarsus through the provision of an orthosis device in the form of a shoe designed to combine the action of manipulation and stretching exercises with the corrective action of a static cast.

Hence, it is an object of the invention to provide a corrective shoe of the character described for the abnormality mentioned, which features an articulated hinge design that enables the shoe to duplicate the manipulative maneuvers necessary for correction of the metatarsal deformity.

It is a further object of the invention to provide a corrective shoe which will be capable of properly stabilizing the heel calcaneous in a neutral position while applying a dynamic corrective force to the forefoot in such a way as to properly abduct the forefoot and minimize metatarsal subluxation and valgus force to the great toe.

In this respect, another feature of the orthosis device or shoe of this invention is its ability to apply a continuous corrective force to the foot while the orthosis is being worn, which force can be adjusted to individual conditions.

Unlike a cast, the orthosis of this invention features easy removal to facilitate skin care and inspection of the skin for potential breakdown, and to allow access to the toes for neurovascular assessment while being worn. In addition, it also provides for a great deal of adjustability to compensate for potential neurovascular compromise.

With these observations and objectives in mind, the manner in which the invention achieves its purposes will be appreciated from the following description and the accompanying drawings which exemplify the invention, it being understood that such changes in the specific apparatus disclosed herein may be made as come within the scope of the appended claims.

The accompanying drawings illustrate two complete examples of the physical embodiments of the invention constructed according to the best modes so far devised for the practical application of the principles thereof, and in which:

FIG. 1 is a perspective of a corrective shoe embodying this invention, showing the outer side of the shoe;

FIG. 2 is a perspective viewing the shoe from its inner side;

FIG. 3 is a perspective viewing the shoe from its front and with the side quarters of the shoe spread apart to show its interior;

FIGS. 4 and 5 are bottom views of the shoe seen in FIGS. 1–3; and

FIG. 6 is a bottom view of a modified embodiment of the invention.

Referring now to the accompanying drawings, the numeral 10 generally designates an orthosis device in the nature of a shoe for a child. The shoe illustrated is of the above ankle type similar to a jodhpur, but differs from the conventional in that it has no toe cap, nor does it have laces or eyelets to hold them. Instead, the shoe features opposite quarters 11 and 12 at its outer and inner sides, respectively, which quarters have open ends or edges 13 that are close together at the top of the shoe at its front, then diverge gradually downwardly and outwardly toward the toe of the shoe where the edges diverge more radically, as at 15, and extend to the sole 16 to define a more or less wide opening at the toe.

Toe and ankle straps 18 and 19 respectively, are cooperable with a third strap 20 that extends up and over the instep to hold the shoe firmly on the foot of a child, with the desired degree of pressure. For that purpose, the toe and ankle straps are provided with cooperating Velcro fastening devices 22 to allow ready adjustment of pressure as well as securement of the shoe to or detachment thereof from the foot of a child. The instep strap, however, is shown as having an ordinary buckle type fastener 23, for the same purpose.

It is to be noted that the instep strap 20 has one end portion 24 secured as by a rivet 25 to the outside of the inner quarter 12 at its lower portion adjacent to the heel 26 of the shoe. This fixed end portion of the strap extends upwardly and forwardly to pass through a slit 27 in the quarter 12 to the underside thereof, where the strap then passes through slits 28 in the tongue 29 of the shoe as seen best in FIG. 3. The free end portion 31 of the instep strap thereafter passes through a slit 32 in the outer quarter 11 from whence it extends downwardly and rearwardly along the outside of the quarter 11 to have its perforated end engaged in the buckle 23.

The upper edges of the quarters are padded as at 34, for comfort to the wearer.

The tongue 29 is not secured to the quarters but is held in place solely by the instep strap 20, so as to be readily self adjusting to the foot of the wearer. In addition, the lower front edge portion of the tongue is serrated and spaced from the insole 37 a distance to accommodate the toes of the wearer, that is to say, to allow the front of the wearer's foot to easily pass thereunder.

The main characteristic of the orthosis device of this invention resides in the fact that the sole 16 of the shoe has an elongated transverse cut 38 therethrough, slightly to the rear of the center of the sole, which cut divides the shoe into relatively movable toe and heel portions 16T and 16H, respectively. The cut 38 extends from a point 39 near to but spaced from the inner edge of the sole, all the way across the sole to its outer edge. The side edges of this cut are normally held in substantially abutting engagement by a strap or elastic band 40, as seen best in FIGS. 1 and 4, but when the maladjusted foot of a child suffering from congenital metatarsus is in place in the shoe, the foot will hold the side edges of the cut in a spread apart condition as seen in FIG. 5 an extent depending upon the degree of deformity of the foot at the time the orthosis device is first employed.

It is essential to this invention that the short uncut portion 42 of the sole 16 adjacent to the end 39 of the cut 38 renders the sole weak enough so that said uncut portion 42 will provide in effect a hinge or pivot that allows the toe portion 16T of the shoe to move back and forth a more or less limited but sufficient extent about a vertical axis, relative to the heel portion 16H.

In order to further assure more or less free movement of the toe portion 16T from its rest position (seen in FIG. 4) in the inward direction (toward the inner quarter 12) to its position of use seen in FIG. 5, a portion of the inner quarter 12 at the sole is notched as at 43 at a location directly adjacent to the hinge defining portion 42 of the sole. In addition, the quarters 11 and 12 of the shoe are provided with generally upright elongated slits 45 and 46, respectively, to further assure such freedom of motion of the toe portion 16T of the shoe relative to the heel portion 16H.

The slit 45 extends all the way down to the sole 16 while the slit 46 terminates just above the notch 43.

The band 40 normally draws the edges of the slit 45 together, and tends to hold the edges of the slit 46 slightly separated so that the latter slit has the appearance of an elongated slot.

The band 40, of course, constitutes a force applying member which can act to apply yielding pressure to a deformed foot in the shoe (as in FIG. 5) tending to move the toe portion 16T of the shoe and the foot therein outwardly toward the outer quarter 11. Hence, the band 40 can be said to at all times yieldingly resist motion of the toe portion 16T inwardly, toward the inner quarter 12, and of course, it tends to at all times move the toe portion 16T outwardly, in the direction to close the cut 38.

The band 40 extends along the outer quarter 11 of the shoe, alongside of and parallel to the sole 16, and has its forward end fixed to said quarter near the front thereof, as at 48. The rear portion 49 of the band is perforated and made of non-stretchable material, for securement in a buckle 50 fixed to the quarter 11 near the heel of the shoe. Like the instep strap 20, the band 40 is thus also adjustable to enable the degree of corrective pressure which it exerts on the foot to be varied as necessary.

Another way of accomplishing this desired application of corrective force to the deformed foot is shown in FIG. 6. As therein seen, rigid levers 54 and 55 of clear plastic or the like, are respectively affixed to the toe and heel portions of the shoe sole as by rivets 56, and are mounted on a common pivot 58 fixed in the sole 16 at a location adjacent to the cut 38' and to the edge of the sole at the inner side of the shoe. In this case, however, the cut 38' can, if desired, extend all the way across the sole.

The levers have lugs 60 that project laterally therefrom toward and beyond the outer edge of the sole 16 to have the ends of a coiled tension spring 61 attached thereto. The spring normally draws the toe portion around on its pivot 58 in the direction toward the outer side of the shoe so as to bring the edges of the cut 38' together.

The spring, of course, yieldingly resists clockwise pivotal motion of the toe portion relative to the heel portion, just as does the elastic band 40 of the first described embodiment of the invention. The spring thus serves the same purpose as the elastic band, although it is replaceable by a stronger spring to provide the adjustment of pressure as treatment of a maladjusted foot in the shoe continues. A sleeve 62 of semi-soft material preferably is employed to enclose the spring.

In both embodiments of the invention, a stiff insert 64 in the interior of the shoe overlies the area encompassing the cut in the sole.

In both cases, however, the strap 40 with its elastic portion and/or its equivalent tensioning device 61 accomplish the desired action of manipulation and stretching exercises with the corrective action of a static cast. This has never before been possible.

Another advantage of the orthosis device of this invention is its ready removability, which, as compared to the past practice of applying a cast to the maladjusted foot, eliminates the dangers entailed in use of a cast saw or the tedium of soaking a cast to facilitate its removal. The expense of repeated casting is also eliminated.

It is also important to observe that the orthosis device of this invention maintains the appearance of a shoe, rather than a cast, so that potential psychological trauma to the patient and the patient's parents is avoided.

Treatment with the orthosis also can be easily enhanced by manipulation and stretching, if so desired by a physician, as the orthosis device is readily removable to enable such manipulation, and then replaceable with whatever adjustment may be necessary to maintain the corrected position.

The orthosis device also avoids potential complications of casting, such as over-stretching or avulsion of the ligaments on the medial side of the foot, or deformity of the cuboid on the lateral side by being squeezed in an over-corrected position.

From the foregoing description, together with the accompanying drawings, it will be readily apparent that the orthosis of this invention fulfills a long standing need for a device which is ideally suited for the treatment of congenital metatarsus.

I claim:

1. An orthosis device for corrective treatment of congenital metatarsus, comprising:
   A. a shoe having toe and heel portions articulated for lateral movement of the toe portion relative to the heel portion, and having a sole to which said toe and heel portions are secured, said sole having a transverse cut therein defining said toe and heel portions and providing for lateral movement of the toe portion toward the outer side of the shoe, relative to the heel portion;
   B. and force applying means connected with said toe and heel portions at the exterior of said outer side of the shoe, for exerting force on said toe portion in a direction parallel to the shoe sole, and tending to draw the toe portion laterally toward the outer side of the shoe relative to the heel portion.

2. The orthosis of claim 1 wherein said means comprises a coiled tension spring.

3. An orthosis device for corrective treatment of congenital metatarsus, comprising:
   A. a shoe of the above ankle type, having a sole and inner and outer quarters at its opposite sides;
   B. toe, ankle and instep straps for holding the shoe upon the foot of a wearer, each of said straps being adjustable;
   C. said shoe having toe and heel portions which are relatively movable laterally relative to one another;
   D. and means connected with said toe and heel portions for exerting yielding pressure upon the toe portion tending to draw the same toward the outer side of the shoe, relative to said heel portion.

4. The orthosis device of claim 3, wherein said toe and heel portions are defined by a cut through the sole extending transversely thereacross from a point near to but spaced from the edge of the sole adjacent to the inner side of the shoe all the way to the opposite edge of the sole; and wherein said cut renders the sole weak enough to provide for such lateral movement of the toe and heel portions relative to one another.

5. The orthosis device of claim 4, further characterized by:
   E. a transverse cut in the sole of the shoe near its mid point, said cut defining said toe and heel portions and extending to the outer edge of the sole;
   F. and means on the sole defining a pivot about which said toe and heel portions can move relative to one another about a vertical axis adjacent to the opposite edge of the sole and substantially in line with said cut.

6. The orthosis device of claim 3 further characterized by:
   E. said shoe having opposite inner and outer side quarters with substantially upright elongated slits therein medially of the ends of the shoe to facilitate said lateral relative movement of the toe and heel portions of the shoe;
   F. and said shoe having a loose tongue which is independent of the shoe quarters and is held in place solely by the instep strap.

7. The orthosis device of claim 4, further characterized by a stiff insert in the interior of the shoe overlying the sole at the area of the cut therein.

8. An orthosis device for corrective treatment of congenital metatarsus, comprising:
   A. a shoe having a sole and having toe and heel portions;
   B. a connection between said toe and heel portions providing for lateral movement of the toe portion relative to the heel portion toward and from the inner side of the shoe;
   C. and means connected with said toe and heel portions of the shoe for exerting yielding pressure upon said toe portion tending to draw the same toward the outer side of the shoe,
       said means being adjustable to enable variation of said yielding pressure and comprising a strap and buckle extending along the outer side of the shoe parallel and adjacent to the shoe sole, and said strap having an elastic portion for exerting said yielding pressure.

* * * * *